United States Patent
Gothjaelpsen et al.

(10) Patent No.: US 6,509,391 B2
(45) Date of Patent: *Jan. 21, 2003

(54) MOULDABLE HYPOALLERGENIC, SUBSTANTIALLY NON-MEMORY PUTTY-LIKE ADHESIVE

(75) Inventors: Laila Busk Gothjaelpsen, Hvidovre (DK); Danuta Ciok, Nivaa (DK)

(73) Assignee: Coloplast A/S, Humlebaek (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/091,557

(22) PCT Filed: Oct. 22, 1997

(86) PCT No.: PCT/DK97/00463

§ 371 (c)(1),
(2), (4) Date: Jun. 22, 1998

(87) PCT Pub. No.: WO98/17329

PCT Pub. Date: Apr. 30, 1998

(65) Prior Publication Data

US 2002/0120032 A1 Aug. 29, 2002

(30) Foreign Application Priority Data

Oct. 22, 1996 (DK) ............................................. 1167/96
Apr. 30, 1997 (DK) ............................................. 0488/97

(51) Int. Cl.$^7$ .......................... C09J 153/02; A61F 13/02
(52) U.S. Cl. ........................ 523/111; 428/127; 523/118; 524/505; 524/487; 604/307; 604/336; 604/355
(58) Field of Search ............................... 523/118, 111; 524/505, 487, 55; 604/336, 307, 355; 428/127

(56) References Cited

U.S. PATENT DOCUMENTS

| | | | | |
|---|---|---|---|---|
| 4,062,361 A | * | 12/1977 | Poulsen ....................... 604/336 |
| 4,204,540 A | | 5/1980 | Cilento et al. ............... 128/283 |
| 4,231,369 A | * | 11/1980 | Sørensen et al. ........... 604/336 |
| 4,367,732 A | * | 1/1983 | Poulsen et al. ............. 604/307 |
| 4,505,976 A | * | 3/1985 | Doehnert et al. ........... 604/336 |
| 4,551,490 A | | 11/1985 | Doyle et al. .................. 524/22 |
| 4,952,618 A | * | 8/1990 | Olsen |
| 5,059,189 A | * | 10/1991 | Cilento et al. ............... 604/336 |
| 5,466,724 A | * | 11/1995 | Volke et al. |
| 5,492,943 A | | 2/1996 | Stempel ....................... 523/111 |
| 5,559,165 A | * | 9/1996 | Paul |
| 5,593,397 A | * | 1/1997 | La Gro ........................ 604/355 |
| 5,814,031 A | * | 9/1998 | Mooney et al. ............. 604/307 |
| 6,026,527 A | * | 2/2000 | Pearce ......................... 428/127 |

FOREIGN PATENT DOCUMENTS

| | | |
|---|---|---|
| EP | 0 048 556 B1 | 12/1984 |
| GB | 2 290 974 A | 1/1996 |

OTHER PUBLICATIONS

Polymer Science Dictionary, Second Edition, Mark Alger, Chapman & Hall pp. 32–33, 1997.*

* cited by examiner

*Primary Examiner*—Peter Szekely
(74) *Attorney, Agent, or Firm*—Jacobson Holman PLLC

(57) ABSTRACT

A mouldable mass of a hypoallergenic, substantially non-memory putty-like adhesive for use in connection with an ostomy appliance, said mass comprising: a) 1 to 20% by weight of a block copolymer having a major content of di-block copolymer, b) to 5 to 60% by weight of a tackifying liquid constituent, and c) 1 to 10% by weight of a waxy constituent has superior quality with respect to cohesion, gives the mass resistance against erosion and at the same time enables the removal of the mass as an integrated unit without leaving residues at the skin.

12 Claims, No Drawings

MOULDABLE HYPOALLERGENIC, SUBSTANTIALLY NON-MEMORY PUTTY-LIKE ADHESIVE

BACKGROUND OF THE INVENTION

1. Field of the Invention

The present invention relates to a mouldable mass for use in connection with an ostomy appliance or fistulas, to a method for preparing such a mouldable mass and to the use of a mouldable mass to provide a smooth surface on which an ostomy appliance is to be applied or for use in connection with fistulas.

2. Description of the Related Art

In connection with surgery for a number of diseases in the gastro-intestinal tract, a consequence is, in many cases, that the colon, the ileum or the urethra has been exposed surgically and the patient is left with an abdominal stoma and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma. Also, in connection with a fistula, the patient will have to rely on an appliance to collect the bodily material emerging from such opening.

Often, a paste is used for filling the area between the stoma or fistula and a mounting gasket, ostomy washer and/or skin barrier or to build up an area on the abdomen around the stoma so as to provide a relatively flat and smooth surface onto which an appliance or skin barrier can be securely attached.

Such paste should have a composition which is sufficiently tacky to secure the appliance or skin barrier to the abdomen, and a cohesion ensuring safe removal thereof without leaving residues on the skin. On the other hand, the paste must not be so sticky that it cannot be easily shaped by the finger or hand without sticking to the finger or hand. Furthermore, the paste must show a sufficient elasticity in order to be able to follow the movements of the patient without slipping on the skin and should also show a great resistance to erosion caused by aggressive exudates from an ostomy in order to minimize the risk of leakage.

Pastes for use for protecting the area of skin between the stoma and an attached appliance, face plate or skin barrier and for providing a smooth abdominal surface around the stoma for attachment of a skin barrier or appliance are known from EP Patent No. EP 0 048 556 B1 and U.S. Pat. No. 4,204,540

Thus, European Patent No. EP 0 048 556 B1 discloses a composition of paste-like consistency useful for protecting and treating the skin contiguous to a stoma in the form of an alcohol based composition including as a film former the partial ester of the polycarboxylic resin formed from vinyl methyl ether and maleic anhydride, one or more hydrocolloid gums, one or more gelling and thickening agents, a plasticizer, and other optional ingredients.

The composition disclosed in EP 0 048 556 B1 suffers from the drawback that it comprises a considerable amount (25% to 45% by weight) of alcohol, ethanol and isopropanol being preferred. When using such a paste, there is only a limited time for forming the paste after the application as the paste cures when exposed to air. Furthermore, the paste shows less attractive physical properties as a considerable amount of alcohol may be trapped in the paste and have an adverse effect on the properties of the adhesive of an ostomy appliance which is placed upon the paste. Still further, the considerable amount of alcohol may irritate the skin and cannot be used on skin which has been sensibilized.

The method of protecting the area of skin between the stoma and an attached appliance, face plate or skin barrier and for providing a smooth abdominal surface around the stoma for attachment of a skin barrier or appliance disclosed in U.S. Pat. No. 4,204,540 comprises shaping and placing around the stoma the shaped mass. The mass comprises a homogeneous mixture of mineral oil, a premix comprising (A) a pressure sensitive adhesive and an optional elastomer wherein the pressure sensitive adhesive is a low molecular weight polyisobutylene and the optional elastomer is a medium molecular weight polyisobutylene or butyl rubber, and (B) a second component which is a mixture of one or more hydrocolloid gums, a cohesive strengthening agent or a mixture of hydrocolloid gums and cohesive strengthening agent wherein the hydrocolloids are up to 40% guar gum, locust bean gum or mixtures thereof and from 0 to 25% pectin, gum karaya or mixtures thereof, and wherein the cohesive strengthening agent is finely divided cellulose, finely divided substantially water insoluble sodium carboxymethyicellulose or finely divided water insoluble starch-acrylonitrile graft copolymer. It is stated that by controlling the amount of mineral oil the resulting composition can easily be shaped according to the particular need. The pressure sensitive adhesive is based on natural or synthetic viscous substances either possessing dry tack by themselves or developing such tack upon the addition of a plasticizer.

The pastes disclosed in U.S. Pat. No. 4,204,540 suffer from the drawback that the shapeability is very dependant of the content of mineral oil. If an insufficient amount of mineral oil is added, the composition will be too tough to shape and if too much mineral oil is added the composition becomes sticky and difficult to handle. Generally, pastes consisting of polyisobutylene, butyl rubber and mineral oil will be very hard, if the content of butyl rubber is high and hence, the paste will be difficult to shape, or it will be very soft and liquid if the content of butyl rubber is low and the content of mineral oil is high.

U.S. Pat. No. 5,492,943 discloses a pressure sensitive adhesive composition including a blend of two viscoelastic adhesive elastomers, specifically, high molecular weight polyisobutylene and a styrene block copolymer, which along with a plasticizer (preferably petrolatum) and a suitable tackifier and antioxidant, form a continuous phase in which hydrocolloids such as sodium carboxymethylcellulose and pectin are dispersed. The adhesive compositions disclosed in U.S. Pat. No. 5,492,943 are stated to be used for wafers for adhering ostomy appliances to the skin and differ from known compositions by completely avoiding the use of low molecular weight polyisobutylene and furthermore by preferably not including gelatin.

BRIEF SUMMARY OF THE INVENTION

It has surprisingly been found that the above-mentioned drawbacks related to known masses are overcome with the mouldable mass of a hypoallergenic, substantially non-memory putty-like adhesive of the invention.

The present invention relates in its broadest aspect to a mouldable mass of a hypoallergenic, substantially non-memory putty-like adhesive for use in connection with fistulas or an ostomy appliance, preferably as a paste for smoothing out a surface on which an ostomy appliance is to be applied.

Furthermore, the invention relates to a method for preparing a mouldable mass of a hypoallergenic, substantially non-memory putty-like adhesive.

Still further, the invention relates to the use of a mouldable mass of a hypoallergenic, substantially non-memory putty-like adhesive for smoothing out a surface on which an ostomy appliance is to be applied.

DETAILED DESCRIPTION OF THE INVENTION

The invention relates to a mouldable mass of a hypoallergenic, substantially non-memory putty-like adhesive for use in connection with an ostomy appliance, said mass comprising a) 1 to 20% by weight of a block copolymer having a major content of di-block copolymer, b) 5 to 60% by weight of a tackifying liquid constituent, and c) 1 to 10% by weight of a waxy constituent.

In a mass according to the invention, the combination of a block copolymer having a major content of di-block copolymer with a tackifying liquid constituent, and a waxy constituent has shown superior quality with respect to cohesion, giving the mass resistance against erosion and at the same time enabling the removal of the mass as an integrated unit without leaving residues at the skin. This will improve the performance of the mass and decrease the nuisance and skin problems experienced by the user if he has to use aggressive agents to remove residues at the skin before applying a substitute ostomy appliance.

The mouldable mass further comprises one or more optional constituents such as petroleum jelly in an amount of up to 20% by weight, polybutylene oil in an amount of up to 30% by weight and/or liquid paraffin in an amount of up to 30% by weight.

The mouldable mass of the invention differs from the masses/pastes disclosed in EP Patent No. EP 0 048 556 B1 and U.S. Pat. Nos. 4,204,540 and 5,492,943 in that a quite different polymeric material and a waxy constituent are used. This enables the avoidance of the need of use of solvents in the mouldable mass according to the invention. Furthermore, the amount of mineral oil needed for plasticizing the block copolymer having a major content of di-block copolymer and the polyisobutylene and/or polybutylene used in the mouldable mass of the invention instead of butyl rubber is considerably lower than the amounts needed in the compositions disclosed in U.S. Pat. No. 4,204,540 and, at the same time, the criticality of the content of mineral oil is avoided. U.S. Pat. No. 5,492,943 discloses a pressure sensitive adhesive composition to be used for wafers for adhering ostomy appliances to the skin. The patent only discloses the suitablility of the compositions for use for preparation of wafers for adhering ostomy appliances to the skin and is silent with respect to the use of the adhesive composition as a paste. The adhesive compositions of the present invention differ from the adhesives known from U.S. Pat. No. 5,492,943 comprising an elastomer blend composed substantially entirely of one or more high molecular weight polyisobutylenes having a molecular weight of about 750,000 to 2,350,000 and one or more styrene block copolymers compositions by including low molecular weight polyisobutylenes or polybutenes and furthermore by including gelatine.

Thus, the compositions of the present invention and the properties rendering the same suitable for use as an ostomy paste are neither taught nor indicated in the above known references.

The block copolymer preferably has a low molecular weight and a high content of di-block component. The molecular weight of the block copolymer is from 20,000 to 150,000, preferably from 30,000 to 100,000. The content of di block copolymer in the blockcoplolymer is preferably above 10%, more preferred above 25% and more preferred above 30%. The content of di block copolymer imparts cohesion to the mass and renders the mouldable mass less elastic than a corresponding mass comprising a tri-block copolymer due to a minor degree of physical crosslinking and imparts to the plasticity or substantially non-memory putty-like characteristics of the mass.

The mouldable masses of the invention comprise a tackifying viscous liquid constituent. The action of the tackifying liquid constituent is to plasticize and tackify the copolymer. Such a plasticizer should be compatible with the copolymer as compatibility with the copolymer ensures that the adhesive may be removed as an integrated unit.

Furthermore, the mouldable masses of the invention comprise a waxy constituent. The role of the waxy constituent is to render the mass plastic and mouldable and impart non-memory characteristics to the mass.

The block copolymer may be a copolymer comprising a block of a relatively hard polymer which may form physical crosslinking and a block of a softer polymer. The constituents of the block copolymer may be the same as are conventionally used for block copolymers such as SBS, SIS or SEBS copolymers, e.g., styrene and butadiene, isoprene or ethylenebutylene copolymers. The preferred copolymer is a SEBS (styrene-ethylenebutylene-styrene copolymer) having a content of di block component above 30%.

The tackifying viscous liquid constituent is preferably a viscous polymeric material being compatible with the block copolymer. The tackifying liquid may be a polybutylene or polyisobutylene and is preferably a saturated component which cannot give rise to chemical crosslinking deteriorating the non-memory putty-like characteristics of the mass. The tackifying liquid component is more preferred a polybutylene and more preferably polyisobutylene. The molecular weight of a tackifying viscous polymeric component is preferably from 10,000 to 120,000 when determined by GPC.

The mouldable mass of the invention may, if required, comprise a further oily plasticiser for plasticizing SEBS and polyisobutylene/polybutylene in order to reduce the elasticity. Such oily plasticizer is suitably a viscous polymeric material having molecular weight from 300 to 10,000 when determined by GPC.

The mouldable mass of the invention may comprise a tackifier increasing the adhesive properties of the composition in order to ensure a good contact between the appliance and the skin. Such a tackifier is preferably a hydrocarbon tackifier homogeneously distributed in the mass. The tackifier is preferably a terpene tackifier resin or a dicyclopentadiene tackifier resin. Especially preferred according to the invention as hydrocarbon tackifier resin are polymers and copolymers of dicyclopentadiene, alpha-pinene and/or beta-pinene.

The waxy component may, e.g., be a mineral wax or petroleum jelly and is most preferred microcrystalline wax being compatible with the preferred block copolymer SEBS.

In accordance with a preferred embodiment of the invention, the mass comprises a hydrocolloid which is able to absorb moisture or liquids from the body and thus to increase the wearing time of the adhesive and thus of the ostomy appliance. A hydrocolloid component may, e.g. be a water absorbing and water swellable component being mixable with the main components of the mass. Any hydrocolloid known per se for ostomy or wound care purposes may be used. The hydrocolloid may, e.g. be sodium carboxymethylcellulose (CMC), hydroxyethylcellulose, pectin, gelatine, guar gum, karaya, locust bean gum, carrageenan, xanthan, or sodium or calcium alginate. A hydrocolloid will typically be present in an amount of from 20 to 70% by weight of the total composition in order to have a sufficient absorbent capacity and still retain the characteristics of the mouldable mass. More preferred, the total amount of hydrocolloids is from 30 to 60%, and preferably the total amount of hydrocolloids is from 45 to 60% by weight.

For some purposes it is suitable also to include smaller amounts of a filler in the mass of the invention which may add to the cohesion and also contribute to the plasticity. Such filler may, e.g. be any filler known per se for ostomy or wound care purposes such as talc, calcium carbonate, china clay, zinc oxide or the like. Such filler may constitute up to 3–20% by weight of the composition.

Still further, the masses according to the invention may optionally comprise further constituents such as emollients, disinfecting agents and/or bactericidal agents known per se for use for ostomy or wound care purposes.

An especially preferred embodiment of the invention is constituted by a mouldable mass comprising SEBS, polybutene, polybutene oil, a tackifier resin, microcrystaline wax, CMC, pectin, gelatine and zinc white.

The mass may preferably be packed in metered amounts, e.g., in a blister pack or as a rod. A rod may be flat or rolled and have a release liner on one or both sides. The product is preferably produced and packed in a bag under aseptic conditions. The embodiment of a mass in the form of a relatively flat rod which is optionally rolled and which is optionally covered with a release liner known per se on one or both sides is considered a further aspect of the invention. A rod may, e.g. comprise an amount of the mass of the invention suitable for one or more applications, The invention also relates to a method for preparing a mouldable mass of a hypoallergenic, substantially non-memory putty-like adhesive for use in connection with an ostomy appliance comprising a) a block copolymer having a major content of di-block copolymer, b) a tackifying liquid constituent, and c) a waxy constituent which method comprises mixing the block copolymer having a major content of di-block copolymer and a part of the tackifying liquid constituent during heating at a temperature from 50 to 200° C., and admixing the remaining part of the tackifying liquid constituent and the waxy constituent .

The mixing is preferably carried out a Z-mixer in which is preferably preheated to a temperature of 160° C. Firstly equal parts of copolymer and tackifying liquid constituent are mixed at 160° C. for 20 minutes in vacuum. Then, the remains of the tackifying liquid constituent is admixed together with the waxy constituent at the same temperature, and a mixing of 10 minutes is carried out for each addition. If hydrocolloids are to be added, the temperature is lowered to below 100° C., preferable at the most 90° C., before addition, and a vacuum is applied during addition and the further mixing for about 15 minutes.

In a further aspect, the invention relates to the use of a mouldable mass of a hypoallergenic, substantially non-memory putty-like adhesive for use in connection with an ostomy appliance comprising a) a block copolymer having a major content of di-block copolymer, b) a tackifying liquid constituent, and c) a waxy constituent as a paste for smoothing out a surface on which an ostomy appliance is to be applied.

The invention is explained more in detail with reference to the below working examples illustrating embodiments of the invention. The examples are not to be considered as limiting of the scope of protection being defined in the appended claims.

MATERIALS AND METHODS

Kraton® G1726 from Shell: Styrene-ethylenebutylene-styrene copolymer (SEBS) having a molecular weight of 45,000 as determined by GPC and a content of di-block copolymer of 70%.

Kraton® D1118 from Shell: Styrene-butadiene-styrene copolymer (SBS) having a molecular weight of 103,000 (GPC) and a content of di-block copolymer of 80%.

Vector® 4114 from Exxon: Styrene-isoprene-styrene copolymer (SIS) having a molecular weight of 133,000 and a content of di-block copolymer of 40%

Vistanex® LM-MH from Exxon: polyisobutylene (PIB) having a molecular weight of 90,000 (GPC).

Wax Total $^{40}\!/\!_{00}$ from TOTAL. Petroleum jelly: Vaselinum Album from Witco Polybutene oil: Hyvis® 10 from BP having a molecular weight of 1,500, Hyvis® 30 from BP having a molecular weight of 3,000.

Polybutene: Hyvis® 2000 from BP having a molecular weight $M_w$ of 30,000

Mineral Oil: PL 500 from Parafluid Mineral Oel

Tackifier resin: Regalite® R91 resin from Hercules or Arkon® P-90 resin from Arakawa Sodium carboxymethylcellulose:

Akucell® AF2881 from Akzo or

Blanose® 9H4XF from Hercules Corp.

Guar gum: Guar Gum FG 200 from Nordisk Gelatine

Pectin:

Pektin LM 12CG Z from Copenhagen Pectin or

Pektin USP/100 from Copenhagen Pectin

Gelatin: Gelatine P.S.98.240.233 from ED. Geistlich Sohne AG

Zinc Oxide: Zinkoxid Pharma from Hoechst AG

A Z mixer Type LKB 025 from Herman-Linden was used.

EXPERIMENTAL PART

EXAMPLE 1.

Preparation of a mouldable mass according to the invention.

100 grams of Kraton® G1726 was used and the amounts of other ingredients used correspond to the composition stated in Table 1.

Equal amounts of Kraton® G1726 (SEBS) and of Vistanex® LM-MH were mixed in a Z Mixer for 20 minutes at 160° C. under a vacuum of 100 mbar. Then, the vacuum was released, the mixing was continued at 160° C. for 10 minutes and the remains of Vistanex® LM-MH, the wax, and petroleum jelly were admixed and mixed for 10 minutes each. Then, the heating was turned off, and guar gum was added at maximum 90° C. under a vacuum of 100 mbar and mixed for 10 minutes. Finally, pectin, gelatine and zinc oxide were admixed at a temperature of 90° C. and mixed for 10 minutes.

The paste is then ready to use and may preferably be packed in metered amounts, e.g. in a blister pack or rod. A rod may be rolled and have a release liner on one or both sides. The product is preferably produced and packed under aseptic conditions.

EXAMPLE 2.

Preparation of a mouldable mass according to the invention.

100 grams of Kraton® G1726 was used and the amounts of other ingredients used correspond to the composition stated in Table 1.

Equal amounts of Kraton® G1726 (SEBS) and Vistanex® LM-MH were mixed in a Z Mixer for 20 minutes at 160° C. under a vacuum of 100 mbar. Then, the vacuum was released, the mixing was continued at 160° C. for 10 minutes and the remains of Vistanex® LM-MH, the wax, and Hyvis® 10 or PL 500 were admixed and mixed for 10 minutes each. Then, the heating was turned off, and guar gum was added at maximum 90° C. under a vacuum of 100 mbar and mixed for 10 minutes. Finally, pectin, gelatine and zinc oxide were admixed at a temperature of 90° C. and mixed for 10 minutes.

The paste is then ready to use and may preferably be packed in metered amounts, e.g. in a blister pack or rod. A rod may be rolled and have a release liner on one or both sides. The product is preferably produced and packed under aseptic conditions.

EXAMPLES 3–5

Preparation of mouldable masses according to the invention.

In the same manner as described in Example 2 above, mouldable masses according to the invention were produced having the compositions stated in the below Table 1:

TABLE 1

Composition of mouldable masses of the invention of Examples 1–5 stated in % by weight

| Component | Example 1 | Example 2 | Example 3 | Example 4 | Example 5 |
|---|---|---|---|---|---|
| SEBS | 5 | 5 | 5 | 10 | 8 |
| PIB | 30 | 15 | 15 | 10 | 18 |
| Microcrystalline wax | 5 | 5 | 5 | 5 | 5 |
| Petroleum jelly | 10 | | | | |
| Polybutene oil, Hyvis® 10 | | 25 | | | |
| Liquid paraffin | | | 25 | 25 | 20 |
| CMC | | | 12 | 20 | 15 |
| Guar Gum | 15 | 20 | | | |
| Pectin | 15 | 10 | 10 | 10 | 8 |
| Gelatine | 18 | 17.5 | 27 | 20 | 23 |
| Zinc white | 2 | 2.5 | 1 | | 3 |

EXAMPLE 6

Preparation of a mouldable mass according to the invention.

Equal amounts of Kraton® G1726 (SEBS) and Hyvis® 2000 were mixed in a Z Mixer for 30 minutes at 160° C. under a vacuum of 100 mbar and the Hyvis® 2000 was added in four parts to ensure homogeneity during the admixing over a period of 20 minutes. Then, the remains of Hyvis® 2000 was added in four parts at 160° C. over 30 minutes and the vacuum was released. The Hyvis® 10 was added in four parts and mixed for 15 minutes. Wax was added and mixed for 10 minutes. Then, the heating was turned off, and guar gum and CMC were added at maximum 90° C. under a vacuum of 100 mbar and mixed for 10 minutes. Finally, pectin, gelatine and zinc oxide were admixed at a temperature of 90° C. and mixed for 10 minutes.

The paste was ready to use and may preferably be packed in metered amounts, e.g. in a blister pack or rod. A rod may be rolled and have a release liner on one or both sides. The product is preferably produced and packed under aseptic conditions.

EXAMPLES 7–8

Preparation of mouldable masses according to the invention.

In the same manner as described in the Example 2 above, mouldable masses according to the invention were produced having the compositions stated in the below Table 2:

TABLE 2

Composition of mouldable masses of the invention of Examples 6–8 stated in % by weight:

| Component | Example 6 | Example 7 | Example 8 |
|---|---|---|---|
| SEBS (Diblock content about 70%) | 5 | | |
| SIS (Diblock content about 40%) | | 5 | |
| SB (Diblock content about 80%) | | | 5 |
| PIB | | 15 | 15 |
| Polybutene ($M_w$ 30.000) | 15 | | |
| Polybutene oil, Hyvis® 10 | 25 | 25 | 25 |
| Microcrystalline wax | 5 | 5 | 5 |
| CMC | 10 | 13 | 25 |
| Guar Gum | 15 | | |
| Pectin | 5 | 10 | 8 |
| Gelatine | 18 | 22 | 15 |
| Zinc white | 2 | 5 | 2 |

EXAMPLES 9–10

Preparation of mouldable masses according to the invention.

Equal amounts of Kraton® G1726 (SEBS) and Hyvis® 2000 were mixed in a Z Mixer for 30 minutes at 160° C. under a vacuum of 100 mbar and the Hyvis® 2000 was added in four parts to ensure homogeneity during the admixing over a period of 20 minutes. Then, the remains of Hyvis® 2000 was added in four parts at 160° C. over 30 minutes and the vacuum was released. The Hyvis® 10 was added in four parts and mixed for 15 minutes. Resin and wax was added and mixed for 10 minutes each. Then, the heating was turned off, and CMC were added at maximum 90° C. under a vacuum of 100 mbar and mixed for 10 minutes. Finally, pectin, gelatine and zinc oxide were admixed at a temperature of 90° C. and mixed for 10 minutes.

The paste was ready to use and may preferably be packed in metered amounts, e.g. in a blister pack or rod. A rod may be rolled and have a release liner on one or both sides. The product is preferably produced and packed under aseptic conditions.

TABLE 3

Composition of mouldable masses of the invention of Examples 9–10 stated in % by weight:

| Component | Example 9 | Example 10 |
|---|---|---|
| SEBS (Diblock content about 70%) | 5 | 5 |
| Polybutene ($M_w$ 30.000) | 10 | 5 |
| Polybutene oil, Hyvis ® 10 | 25 | 25 |
| Resin | 5 | 10 |
| Microcrystalline wax | 5 | 5 |
| CMC | 15 | 15 |
| Pectin | 10 | 10 |
| Gelatine | 24 | 24 |
| Zinc white | 1 | 1 |

EXAMPLES 11–12

Preparation of mouldable masses according to the invention.

In the same manner as described in the Example 6 above, mouldable masses according to the invention were produced having the compositions stated in the below Table 4.

TABLE 4

Composition of mouldable masses of the invention of Examples 11–13 stated in % by weight:

| Component | Example 11 | Example 12 | Example 13 |
|---|---|---|---|
| SEBS (Diblock content about 70%) | 5 | 5 | 5 |
| Polybutene ($M_w$ 30.000) | 15 | 15 | 20 |
| Polybutene oil, Hyvis ® 10 or 30* | 25 | 25 | 20 |
| Amorphous polyolefin wax | 2.5 | 5 | 2.5 |
| Microcrystalline wax | 2.5 | | 2.5 |
| CMC | 20 | 20 | 20 |
| Pectin | 10 | 12 | 10.5 |
| Gelatine | 19 | 17.5 | 19 |
| Zinc white | 1 | 0.5 | 0.5 |

In Examples 11–12, Hyvis ® 10 was used and in Example 13, Hyvis ® 30 was used.

EXAMPLE 13

Preparation of a mouldable mass according to the invention.

100 grams of Kraton® G1726 was used and the amounts of other ingredients used correspond to the composition stated in Table 4.

Equal amounts of Kraton® G1726 (SEBS) and Hyvis® 2000 were mixed in a Z Mixer for 1½ hours at 160° C. under a vacuum of 100 mbar and the Hyvis® 2000 was added in four parts to ensure homogeneity during the admixing over a period of 20 minutes. Then, the remains of Hyvis® 2000 was added in four parts and wax was at 160° C. over 3 hours and the vacuum was released. Then, the heating was turned off, and Hyvis ® 30 and CMC were added over 15 minutes at maximum 60° C. under a vacuum of 100 mbar and mixed for 1 hour. Finally, pectin, gelatine and zinc oxide were admixed at a temperature of 60° C. and mixed for 10 minutes.

The paste was ready to use and may preferably be packed in metered amounts. The product is preferably produced and packed under aseptic conditions.

What is claimed is:

1. A mouldable mass of a hypoallergenic, substantially non-memory adhesive having the consistency of putty and useful with an ostomy appliance, the mass comprising:

a) 1 to 20% by weight of a styrene block copolymer having a molecular weight, determined by GPC, of from 20,000 to 150,000 and having a content of corresponding di-block copolymer above 25%;

b) 5 to 60% by weight of a tackifying liquid constituent in the form of a viscous polymeric material which is compatible with the block copolymer;

c) 1 to 10% by weight of a constituent which is like wax in nature or appearance; and d) a hydrocolloid.

2. The mouldable mass as claimed in claim 1, wherein the mass further comprises an unctuous plasticizer.

3. The mouldable mass as claimed in claim 1, wherein the mass further comprises, in addition to the tackifying liquid constituent, a hydrocarbon tackifier resin for increasing the adhesive properties of the mass.

4. The mouldable mass as claimed in claim 1, wherein the mass further comprises a filler.

5. The mouldable mass as claimed in claim 1, wherein the mass comprises a member selected from the group consisting of an emollient, a disinfecting agent and a bactericidal agent.

6. A method for preparing a mouldable mass as claimed in claim 1, which method comprises mixing the block copolymer and a part of the tackifying liquid constituent during heating at a temperature from about 50 to 200° C., admixing the remaining part of the tackifying liquid constituent and the constituent which is like wax in nature or appearance, and admixing the hydrocolloid after reducing the temperature to below 100° C.

7. A method of using a mouldable mass as claimed in claim 1, which method comprises applying the mouldable mass to skin around a stoma to provide a plain surface for placing an ostomy appliance.

8. The mouldable mass as claimed in claim 1, wherein the tackifying liquid constituent has a molecular weight of 10,000 to 120,000 determined by GPC.

9. A mouldable mass as claimed in claim 3, wherein the hydrocarbon tackifier resin is a polymer or copolymer of a member selected from the group consisting of dicyclopentadiene, alpha-pinene and beta-pinene.

10. A mouldable mass as claimed in claim 1, wherein the styrene block copolymer is a copolymer selected from the group consisting of styrene-ethylenebutylene-styrene, styrene-butadiene-styrene and styrene-isoprene-styrene.

11. A method as claimed in claim 6, wherein the styrene block copolymer is a copolymer selected from the group consisting of styrene-ethylenebutylene-styrene, styrene-butadiene-styrene and styrene-isoprene-styrene.

12. A method as claimed in claim 7 wherein the styrene block copolymer is a copolymer selected from the group consisting of styrene-ethylenebutylene-styrene, styrene-butadiene-styrene and styrene-isoprene-styrene.

* * * * *